United States Patent [19]

Chabbert

[11] Patent Number: 5,020,226
[45] Date of Patent: Jun. 4, 1991

[54] CAST CUTTER AND METHOD

[75] Inventor: Jean-Paul Chabbert, Venerque, France

[73] Assignee: Societe Laboratoires 3M Sante, Pithiviers, France

[21] Appl. No.: 516,448

[22] Filed: Apr. 30, 1990

[51] Int. Cl.⁵ .................. B23D 45/16; A61B 17/32
[52] U.S. Cl. ................................. 30/390; 30/373; 128/91 A
[58] Field of Search ............... 30/167, 287, 390, 373; 128/90, 91 A; 606/138, 176, 180, 172

[56] References Cited

U.S. PATENT DOCUMENTS

| 590,163 | 9/1897 | Pearson . | |
|---|---|---|---|
| 1,269,373 | 6/1918 | Brinck . | |
| 1,530,023 | 3/1925 | Walton | 30/390 |
| 2,015,535 | 8/1935 | Sacrey | 128/91 A |
| 2,084,488 | 6/1937 | Heller | 128/91 A |
| 2,217,923 | 10/1940 | Silverman | 128/91 A |
| 2,232,733 | 2/1941 | Scarboro | 30/167 |
| 2,344,262 | 3/1944 | Odierna et al. | 30/167 |
| 2,366,017 | 12/1944 | Fortune | 30/167 |
| 2,522,006 | 9/1950 | Wilcox | 30/390 |
| 2,571,527 | 10/1951 | Boyer | 30/167 |
| 2,674,027 | 4/1954 | Kosinski | 30/390 |
| 3,365,798 | 1/1968 | Cunningham | 30/287 |
| 4,290,424 | 9/1981 | Wahl et al. | 128/91 |
| 4,411,067 | 10/1983 | Kirk | 128/91 A |
| 4,418,890 | 12/1983 | Knight | 254/104 |
| 4,421,111 | 12/1983 | Rothman | 128/91 |
| 4,502,479 | 3/1985 | Garwood et al. | 128/90 |
| 4,543,718 | 10/1985 | Duescher | 30/124 |
| 4,609,578 | 9/1986 | Reed | 428/76 |
| 4,611,585 | 9/1986 | Steidle | 128/91 |
| 4,625,405 | 12/1986 | Hudnutt et al. | 30/390 |
| 4,637,391 | 1/1987 | Schlein | 128/317 |
| 4,667,661 | 5/1987 | Scholz et al. | 128/90 |
| 4,705,840 | 11/1987 | Buckanin | 528/53 |
| 4,774,937 | 10/1988 | Scholz et al. | 128/90 |

FOREIGN PATENT DOCUMENTS

| 48159 | 11/1888 | Fed. Rep. of Germany . |
| 437169 | 11/1926 | Fed. Rep. of Germany . |
| 3342918 | 6/1985 | Fed. Rep. of Germany . |
| 2283663 | 4/1976 | France . |
| 2514637 | 4/1983 | France . |
| 116910 | 10/1926 | Switzerland . |
| 531802 | 1/1941 | United Kingdom . |
| 2003391 | 3/1979 | United Kingdom . |
| 2068829 | 8/1981 | United Kingdom . |

Primary Examiner—Douglas D. Watts
Assistant Examiner—Paul M. Heyrana, Sr.
Attorney, Agent, or Firm—Gary L. Griswold; Walter N. Kirn; Stephen W. Bauer

[57] ABSTRACT

An assembly and method for cutting through a cast of the type having flexible wrapping and a rigid outer shell. The assembly comprises a side plate having edges defining an elongate notch for receiving the cast, a cutting blade rotatably mounted on the side plate adjacent the notch, and means for rotating the cutting blade relative to the side plate. The edges of the side plate defining the notch include at least one cutting portion. The cutting blade is maintained in sliding scissors-like engagement with the cutting portion of the side plate to shear the cast between the cutting portion and the cutting blade as the blade is rotated.

12 Claims, 4 Drawing Sheets

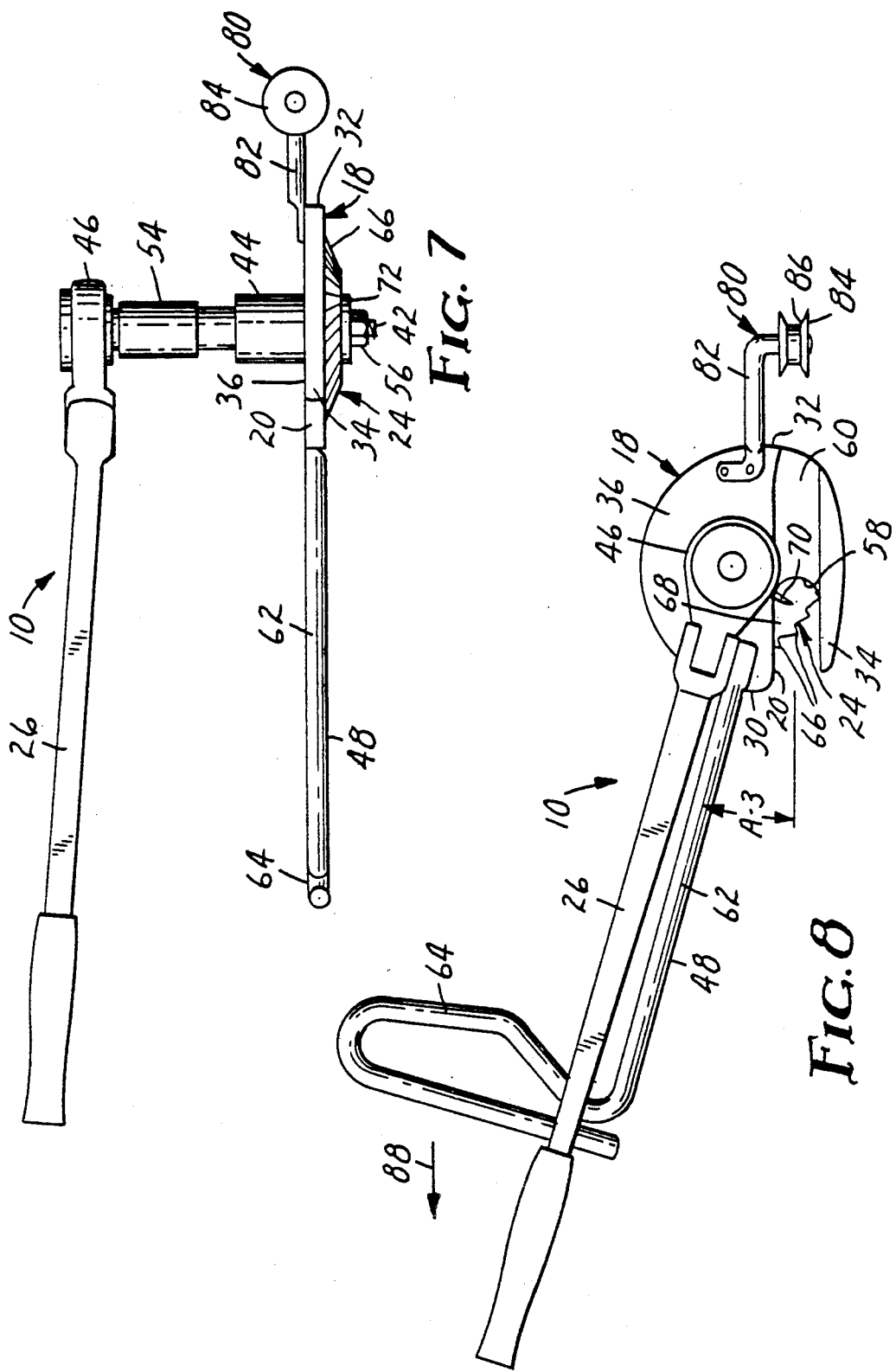

CAST CUTTER AND METHOD

This invention relates generally to a cutter, and more particularly to a cast cutter that is adapted to cut through a cast of the type having a rigid shell and soft or flexible wrapping underlying the shell.

BACKGROUND OF THE INVENTION

Casts of the type used to set broken bones, for example, are made of plaster, as well as various synthetic resin materials, such as the fiberglass/resin composite sold under the trademark "SCOTCHCAST" by the Minnesota Mining and Manufacturing Company of St. Paul, Minn. U.S.A., and/or described, for example, in U.S. Pat. Nos. 4,502,479; 4,609,578; 4,667,661; 4,705,840 and 4,774,937. Advantages of fiberglass/resin composite materials include gas permeability, light weight, and transparency to X-rays.

Casts ordinarily consist of a tubular stockinet or an elongate strip or bandage that is placed or wrapped, for example, around a patients injured limb, a layer of synthetic cast padding wrapped around the stockinet, and a plurality of layers of the fiberglass-resin composite or plaster material wrapped around the padding to form a rigid shell. Such cast padding and stockinet is typically made from very flexible woven or nonwoven materials, such as cotton, polyester or other fibers. Cast padding and stockinet will sometimes be collectively referred to herein as "wrapping".

Cast shells have typically been removed by using powered oscillating saws, which are noisy and may create a substantial quantity of dust. In order to prevent injury to the patient, these saws are usually adapted to be oscillated at a high frequency and low amplitude. Despite that precaution, the saw can cause burns or cuts in some situations, and notwithstanding any actual danger, patients, especially small children, may be frightened by the saw. U.S. Pat. No. 4,637,391 (Schlein) describes a surgical saw blade for cutting plaster or fiberglass casts. That saw blade is adapted to oscillate at high frequency (e.g., 12,000–14,000 oscillations per minute) and low amplitude. An adjustable depth stop is provided to limit the depth that the saw blade may cut.

U.S. Pat. No. 4,421,111 (Rothman) describes a surgical cast cutter that includes a saw blade that is oscillated at low amplitude to prevent injury of the patient. That cutter includes the feature of vacuum exhaust of dust particles created in cutting the cast. British Patent No. 2 068 829 (Saito) and U.S. Pat. No. 4,543,718 (Duescher) describe other cast cutters employing oscillatory motion and vacuum exhaust of dust particles.

In addition to the creation of dust, one problem with oscillating cast cutters is that typically they do not cut through the soft layers or wrapping of the cast. This is because the low amplitude, high frequency motion of the blade is usually ineffective against soft tissue or fabric. As a result, the soft layers or wrappings underlying the cast are typically removed as a separate step after cutting the cast. For example, U.S. Pat. No. 3,365,798 (Cunningham) describes a device for cutting the soft wrappings underlying plaster casts after the shell has been cut. That device includes a shoe which may be positioned between the wrappings and the patient and two inwardly-facing intersecting blades that cut the wrapping as the device is pushed or pulled through a slot cut in the cast.

Another method of protecting a patient from the saw blade of a cast cutter has been to place a guard between the patient and the saw blade. For example, U.S. Pat. Nos. 2,344,262 (Odierna et al.) and 2,366,017 (Fortune) describe powered cast cutters including a guard or shoe for protecting the patient from the saw blade, with the guard or shoe separating the saw blade from the patient's skin. The shoe of those cutters are placed under the cast (i.e., between the cast and the patient's skin).

U.S. Pat. No. 590,163 (Pearson) describes a manually operated cast cutting tool having a guard for protecting the patient from the saw blade. That guard includes a foot that is positioned between the cast and the flesh of the patient. A crank-arm is provided for manually rotating the saw blade. U.S. Pat. No. 2,571,527 (Boyer) shows another cast cutter having a guard that is placed between the cast and the patient. U.S. Pat. No. 2,217,923 (Silverman) shows powered and manually operated cast saws that include a guide shoe having a semi-circular groove for receiving the saw blade to accommodate different thicknesses of casts.

U.S. Pat. No. 1,269,373 (Brinck) describes a cutting device having a shield plate that is slipped between the cast and the patient, and a circular cutting member that is movable relative to the shield plate as the cast is cut. That device includes a crank for rotating the cutting member, and a pin to limit motion of the cutting member toward the shield plate as the cast is cut.

U.S. Pat. No. 2,232,733 (Scarboro) shows a powered cast remover that includes a guard that separates the saw blade from the patient and a suction fan for removing the cuttings and placing them in a container.

While cast cutting devices that employ a guard between the cast and the patient and a conventional rotary saw blade may efficiently, quietly and safely cut the rigid shell of the cast, it has been found that they are ineffective at cutting the flexible wrappings underlying the shell. The wrappings are frequently caught by the teeth of the saw blade and wrapped around the axle of the saw blade, with the result that such devices have typically become jammed on the cast shortly after starting the cut (e.g., within 4–6 inches (100–150 mm)).

U.S. Pat. No. 4,611,585 (Steidle) describes a cast cutter that includes a fixed center blade that is positioned between the cast and patient and two motor-driven oscillating blades disposed along opposite sides of the center blade. That cutter includes a movable cover hood which apparently ensures that the blades are only exposed when the blades are applied to the plaster cast itself.

Casts have also been cut by embedding wire in the cast material when forming the cast, and pulling the wire to cut the cast. For example, U.S. Pat. No. 4,290,424 (Wahl et al.) and British Patent No. 2 003 391 (Lampke et al.) show cutting wires that are embedded in the material of the cast. See, also, West German Patent No. 3 342 918 (Strang).

SUMMARY OF THE INVENTION

An assembly of the invention is designed to cut completely through a cast of the type typically having flexible wrapping(s) and a rigid shell in a single cutting operation. Among other things, the assembly is designed to reduce the production of "saw dust" when cutting casts, and preferably to be driven by manual power.

Generally, the assembly comprises a side plate having edges defining an elongate notch for receiving the cast, and a cutting blade rotatably mounted on the side plate generally adjacent the notch. The side plate's edges defining the notch include at least one cutting portion, and the cutting blade is maintained in sliding scissors-like engagement with the cutting portion of the side plate to shear the wrapping and shell between the cutting portion and the cutting blade as the cutting blade is rotated. Means is provided for rotating the cutting blade relative to the cutting portion of the side plate.

Preferably, the cutting blade is adapted to both cut through the rigid shell by removing material from the shell with the action of a saw blade and to shear through the soft or flexible wrappings underlying the shell, and possibly a portion of the shell, in a manner similar to the action of scissors.

The method according to the invention generally comprises maintaining the cutting blade of the assembly in sliding scissors-like engagement with the cutting portion of the side plate, and introducing a portion of the cast into the notch of the side plate and into contact with the cutting blade, with a portion of the side plate separating the cutting blade from the patient. The cutting blade is then rotated relative to the cutting portion of the side plate to shear the wrapping and shell between the cutting portion and cutting blade, and the apparatus is advanced through the cast as the cutting blade is shearing the cast. Finally, the cast is removed from the patient's limb after the cast has been cut.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 7 is a bottom plan view of the assembly of FIGS. 1-5, showing a cast separator mounted on the assembly;

FIG. 8 is a left side elevation of the assembly and cast separator of FIG. 7.

DETAILED DESCRIPTION OF PREFERRED EMBODIMENTS

Figures 1, 9:
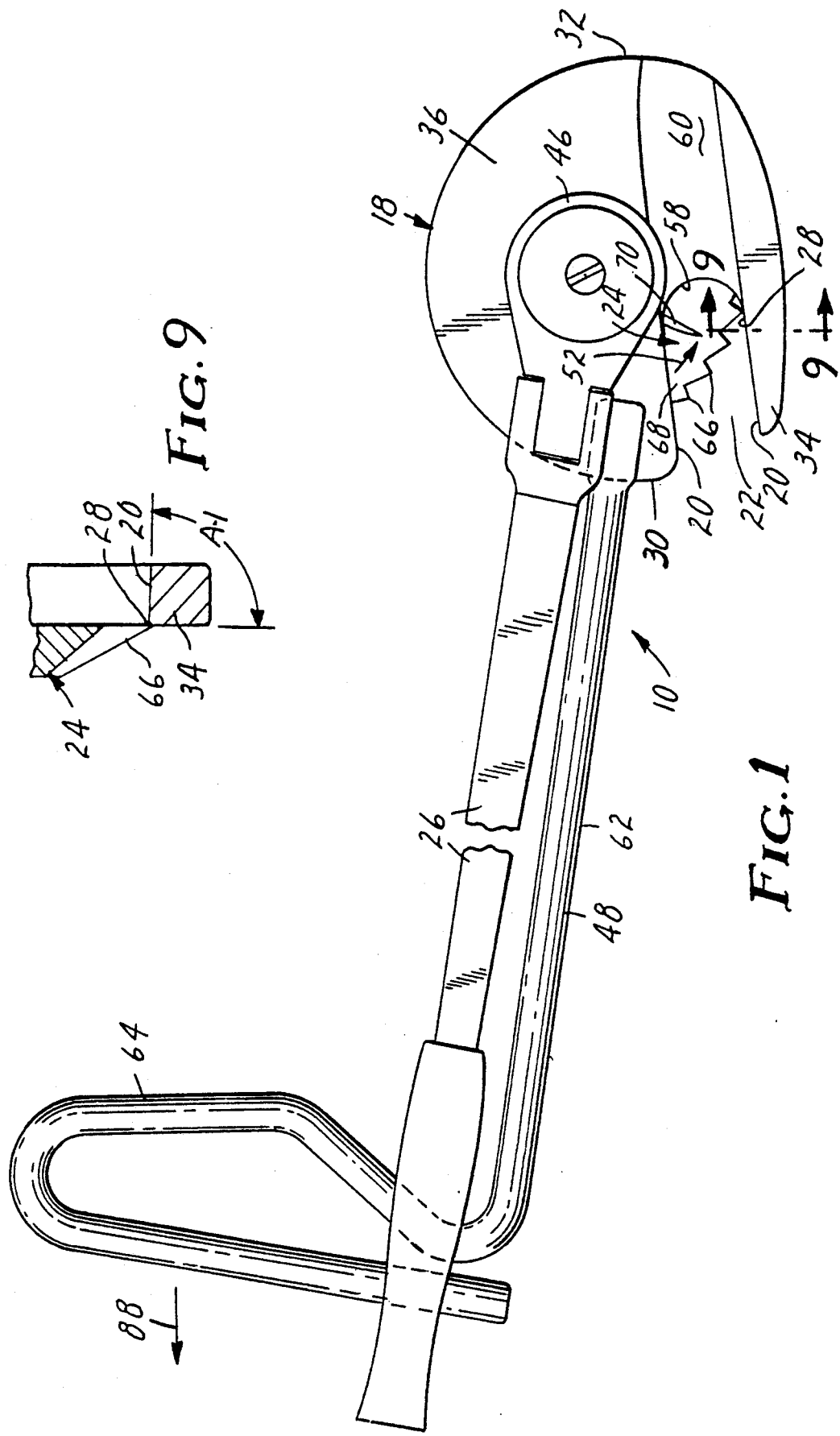
FIG. 1 is a left side elevation of an assembly of the invention.
FIG. 9 is a cross-sectional view substantially along line 9—9 of FIG. 1, illustrating a guard or finger of the side plate.

An assembly of the invention is indicated generally by the reference numeral 10, and is adapted for cutting through a cast 12 of the type typically having flexible wrapping 14 and a rigid shell 16. As used herein, "wrapping" refers to any type of soft or flexible material that underlies the shell 16 of a cast 12, and typically includes a layer of stockinet and a layer of padding of polyester woven, knit or nonwoven material.

As shown in FIG. 1, the assembly 10 generally comprises a side plate 18 having edges generally designated 20 defining an elongate notch 22 for receiving the cast 12, and a cutting blade 24 rotatably mounted on the side plate 18 adjacent the notch 22. Means (e.g., crank arm 26) is provided for rotating the cutting blade 24 relative to the side plate 18. The edges 20 defining the notch 22 include at least one cutting portion 28. The cutting blade 24 is maintained in sliding scissors-like engagement with the cutting portion 28 of the side plate 18 to shear the wrapping 14 and shell 16 between the cutting portion 28 and the cutting blade 24 as the cutting blade 24 is rotated.

Figure 3:
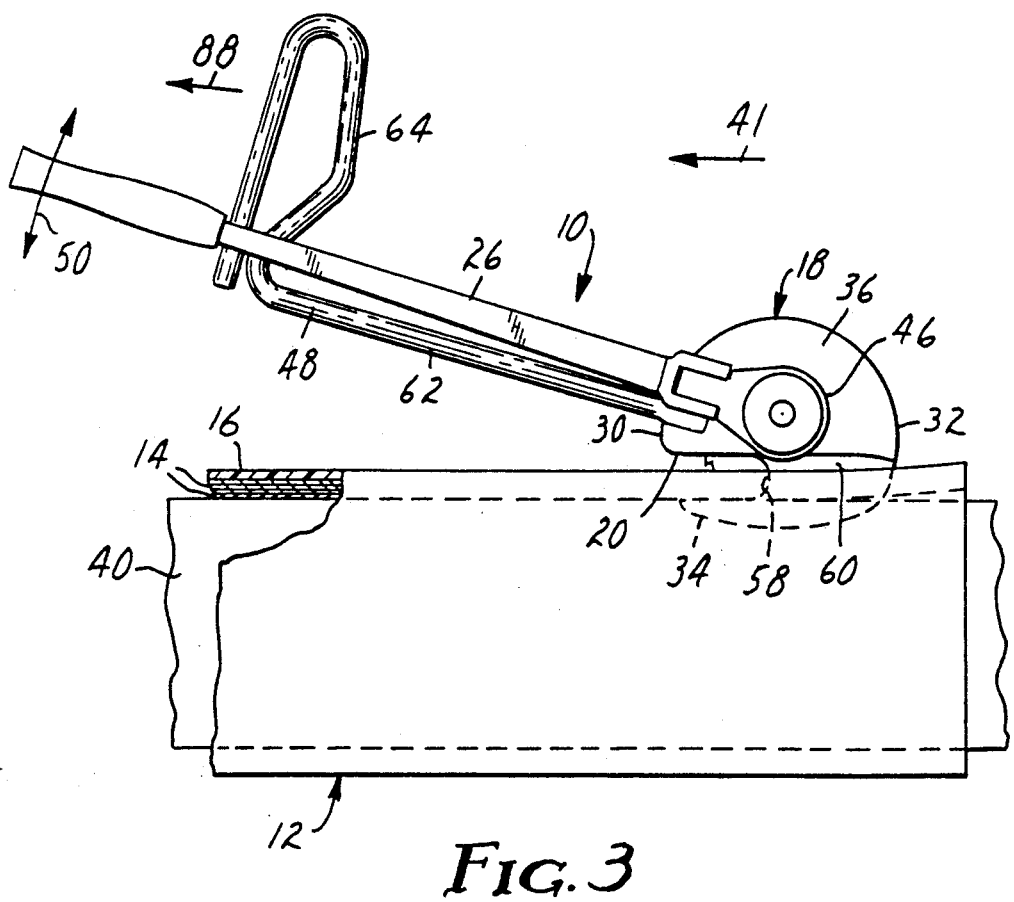
FIG. 3 is a left side elevation of the assembly of FIGS. 1 and 2, illustrating cutting a cast with the assembly.

More specifically, the side plate 18 has forward and rearward ends 30 and 32, and a finger 34 extending generally forwardly from the body 36 of the side plate 18. An edge 28 of the finger 34 forms the cutting portion 28 of the side plate 18. As shown in FIG. 9, the cutting portion 28 of the edge 28 is smooth and sharp, and preferably formed at an angle A-1 only slightly less than ninety degrees (e.g., 87-89 degrees). As illustrated in FIG. 3, the finger 34 is adapted to be placed between the wrapping 14 of the cast 12 and the patient 40 to protect the patient 40 from the cutting blade 24 and to facilitate tensioning and shearing the wrapping 14 between the cutting portion 28 and the teeth 66 of the cutting blade 24.

The "left" major surface of the side plate 18, which is the surface in sliding engagement with the cutting blade 24, is substantially flat and smooth. The words "right", "left", "rightwardly" and "leftwardly" are used herein merely for convenience, and are used in reference to the intended direction of motion of the assembly 10 indicated by the arrow 41 in the figures. "Rightwardly" refers to the upward direction in FIG. 2, and "leftwardly" refers to the downward direction in FIG. 3. "Forward" or "forwardly" refer to the direction indicated by the arrow 41 in FIG. 3, and "rearward" or "rearwardly" refer to the direction opposite the arrow 41.

The means for rotating the cutting blade 24 preferably comprises the manually operable crank arm 26 shown in FIGS. 1-3, 7 and 8, although a powered drive motor (not shown) or any other suitable drive mechanism could alternatively be provided for rotating the cutting blade 24. An axle 42 is rotatably mounted through a self-lubricating bearing or bushing 44 in the side plate 18. The cutting blade 24 is mounted adjacent one end of the axle 42, and the crank arm 26 is releasably mountable on the axle 42 adjacent the other end thereof. The bushing 44 and the axle 42 are preferably formed of dissimilar metals to reduce frictional wear between the axle 42 and bushing 44. For example, the bushing 44 may be formed of brass, and the axle 42 formed of hardened steel. The bushing 44 may be either press fit or threadably received in a bore through the side plate 18.

Most preferably, the crank arm 26 includes a ratchet mechanism 46 so that the crank arm 26 may be ratcheted relative to the axle 42 to rotate the axle 42 and cutting blade 24, and a handle 48 is provided extending forwardly from the side plate 18 to facilitate operation of the crank arm 26 and pulling the side plate 18 forwardly through the cast 12 as the crank arm 26 is operated.

Figure 2:
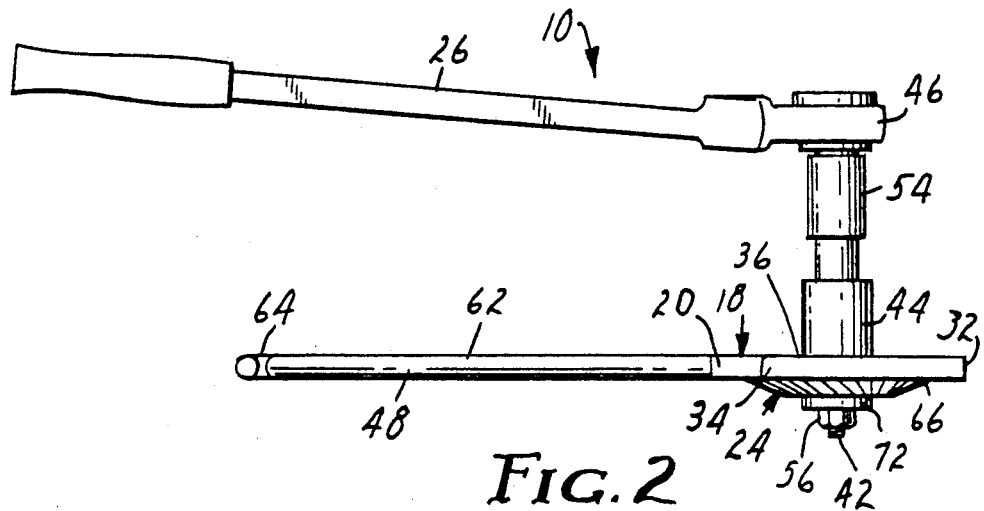
FIG. 2 is a top plan of the assembly of FIG. 1.

As shown in FIGS. 1-3, the crank arm 26 and ratchet mechanism 46 may take the form of a conventional socket wrench (at 26). A wrench of this type typically has an offset handle (at 26), a four-sided male drive piece (not shown), and the ratchet mechanism 46 for ensuring that the drive piece rotates in only one direction as the handle 26 is reciprocated as indicated by the arrow designated 50 in FIG. 3. The ratchet mechanism 46 may be of the type that can be adjusted to reverse the action of the mechanism 46 to permit rotating the drive piece in the other direction, although a ratchet mechanism 46 that can only be driven in one direction is preferred (e.g. for clockwise rotation of the cutting blade 24 as indicated by arrow 52 in FIGS. 1 and 8).

A spring-loaded bearing (not shown) is spring biased laterally outwardly from the drive piece of the crank arm 26 to securely and releasably mount a conventional socket 54 (FIG. 2) on the drive piece. An elongate extension or rod (not shown) may be provided between the drive piece and the socket 54 in the event that movement of the crank arm 26 would otherwise be restricted. A plurality (e.g., 4-6) of such extension rods of various lengths may be provided with the assembly 10, with the operator of the assembly 10 selecting the appropriate extension rod and mounting it between the socket 54 and the drive piece of the crank arm 26.

The right end of the axle 42 (the upper end in FIG. 2) is tightly and securely received in the socket 54, and preferably has a polygonal (e.g., hexagonal) configuration complementary to a polygonal (hexagonal) cavity in the socket 54. The socket 54 may be permanently or semi-permanently mounted on the right end of the axle 42, for example, by an "Allen" or internal "hex" head bolt received in a coaxial threaded bore in the axle 42.

The axle 42 preferably includes an enlarged diameter cylindrical portion (not shown) and a smaller diameter cylindrical portion (not shown) extending coaxially leftwardly from the enlarged portion (in the direction toward the cutting blade 24), with both the enlarged and smaller diameter portions being rotatably received in the bore of the bushing 44. The left shoulder (not shown) of the enlarged portion of the axle 42 and a complementary shoulder in the bore of the bushing 44 prevent axial movement of the axle 42 in the leftward direction away from the socket 54 (downwardly in FIG. 2). The smaller diameter cylindrical portion is housed in the portion of the bushing 44 that is received in the side plate 18.

The cutting blade 24 is mounted on a polygonally-shaped mounting portion of the axle 42 that extends axially leftwardly (downwardly in FIG. 2) from the smaller diameter cylindrical portion of the axle 42. Most preferably, the mounting portion of the axle 42 has a generally square-shaped cross section that corresponds to a square-shaped opening through the center of the cutting blade 24, and a threaded left end portion extends axially outwardly from the square-shaped portion for threadably receiving a conventional lock nut 56 or other suitable fastener. The cutting blade 24 and/or the lock nut 56 prevent axial movement of the axle 42 in the rightward direction toward the socket 54 (upwardly in FIG. 2).

The cutting blade 24 and axle 42 may alternatively be formed in one integral piece, in which case the configuration of the axle 42 would be changed to permit assembly. As used herein, "integral" and "one piece construction" refer to a single part that is manufactured in a single continuous piece, as opposed to parts that are assembled from component parts. The axle and drive piece (not shown) of the ratchet mechanism may also be integrally formed as one continuous piece, in which case the socket 54 would be eliminated from the assembly.

Regardless of the particular construction of the axle 42 and cutting blade 24, it is desirable that they be rigidly fixed or connected together so that the desired relationship can be maintained between the cutting blade 24 and the side plate 18. In this regard, it may also be noted that the internal shoulder (not shown) of the bushing 44 and the "left" shoulder of the enlarged cylindrical portion of the axle 24 prevent the cutting blade 24 from moving away from the side plate 18. Alternatively or in addition, the central hub portion 72 of the cutting blade 24 may be spring biased toward the side plate 18 to help maintain the cutting blade 24 in engagement with the cutting portion 28 of the side plate 18.

As shown in FIG. 1, the notch-defining edges 20 of the side plate 18 are generally U-shaped in side elevation, with generally parallel "legs" or edge portions (also at 20) extending generally forwardly from an arcuate end portion 58 to the forward end 30 of the side plate 18. The arcuate end portion 58 is positioned generally adjacent and below the axle 42 so that a portion of the cutting blade 24 is exposed through the notch 22. The elongate notch 22 and finger 34 may have lengths, for example, of approximately 30 mm between the arcuate end portion 58 and the forward end 30 of the side plate 18. The distance between the parallel edge portions 20 is sufficient to permit the cast 12, including the shell 16 and wrapping 14, to be placed through the notch 22 against the cutting blade 24. For example, the distance between these parallel edge portions 22 may be approximately 17 mm.

An arcuate channel 60 is formed in the right side of the side plate 18 between the arcuate end portion 58 and the rearward end 32 of the side plate 18. The channel 60 is tapered outwardly in the rearward direction (rightwardly in FIGS. 1 and 5) from the notch 22 to the rearward end 32 of the side plate 18. For example, the arcuate channel 60 may be tapered at an angle A-2 of approximately 10 degrees.

The taper of the arcuate channel 60 facilitates separating cut portions of the cast 12 by acting as a wedge to wedge the cut portions apart as the assembly 10 is advanced through the cast 12. This wedge-action of the channel 60 is believed to help prevent binding of the cutting blade 24 in the cast 12. The arcuate walls of the channel 60 also help guide the assembly 10 through the cast 12. More specifically, the walls of the channel 60 are preferably parallel to one another and spaced apart a distance substantially equal to the distance between the parallel edge portions 22. The walls of the arcuate channel 60 extend linearly rearwardly (rightwardly in FIGS. 1 and 8) from the parallel edge portions 22 of the notch 20, and the surfaces forming the channel 60 are smoothly contoured in order to facilitate movement of the cut portions of the cast 12 along the channel 60.

As illustrated in FIG. 8, the longitudinal axis of the column 62 of the handle 48 may be conveniently offset at an angle A-3 of approximately ten degrees from the common longitudinal axis of the notch 20 and arcuate channel 60. While other orientations of the handle 48 relative to the notch 20 and arcuate channel 60 may be employed, the illustrated orientation is believed to be ergonomically effective in facilitating travel of the assembly 10, especially of the finger 34, through the cast 12. The handle 48 preferably includes an ergonomically configured grip portion 64 extending generally perpendicularly from the forward end of the column 62 (leftward in FIG. 1).

Figure 4:
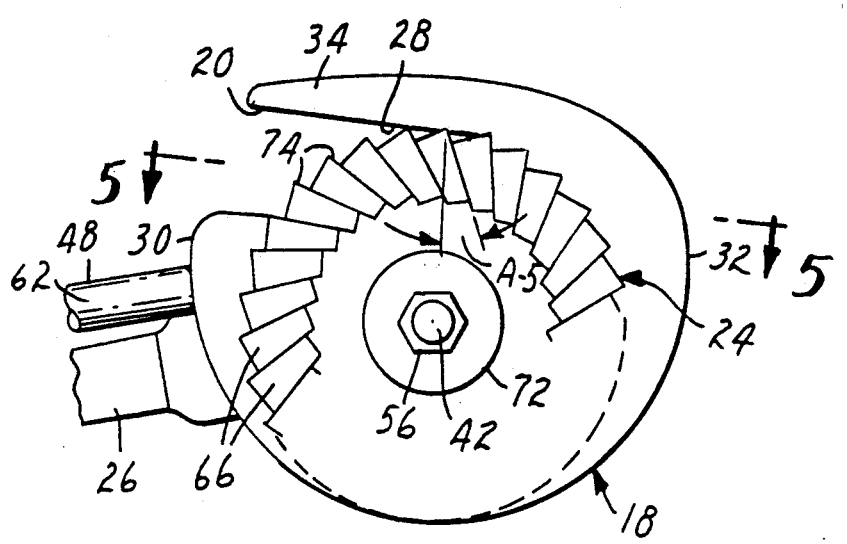
FIG. 4 is a right side elevation of a side plate of the assembly of FIGS. 1-3.
Figure 5:
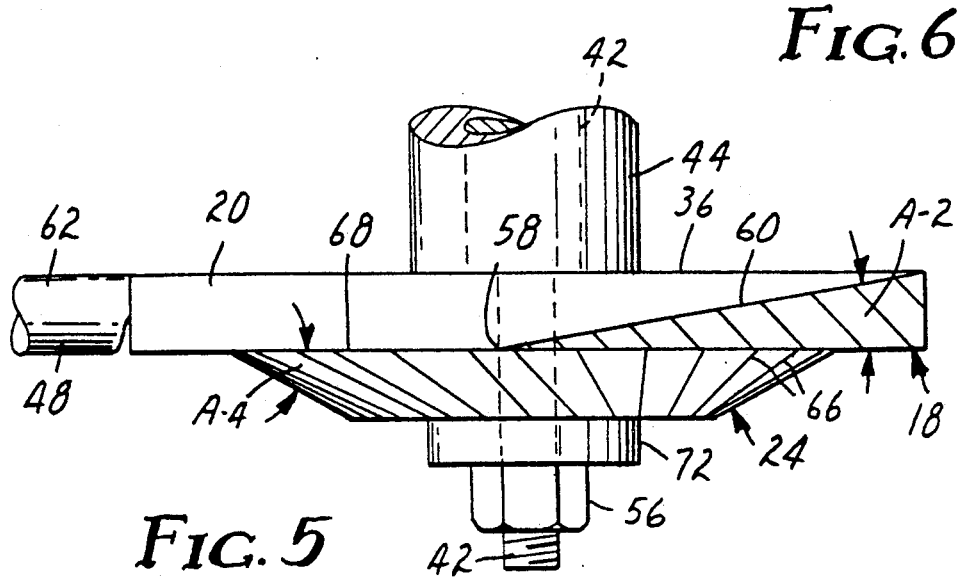
FIG. 5 is a cross-sectional view substantially along line 5—5 in FIG. 4.

As illustrated in FIGS. 4 and 5, the cutting blade 24 is preferably of generally conical or frustoconical configuration, and includes a plurality of generally radially outwardly extending teeth 66. The "base" 68 of the conical or frustoconical blade 24 provides a substantially flat surface (also 68) in sliding engagement with the substantially flat right major surface of the side plate 18.

At least one, but preferably three to five elongate recesses (e.g., recess 70 in FIG. 1), are formed in the base 68 of the cutting blade 24. These recesses 70 are adapted to receive small amounts of cast dust or loose material to prevent jamming of the cutting blade 24. Alternatively, "cut-outs" or recesses (not shown) may be provided in the right major surface of the side plate 18.

The teeth 66 of the cutting blade 24 are shown in the drawing (e.g., FIG. 5) as being tapered in the radially outward direction toward the base 68. For example, the teeth 66 may be tapered at an angle A-4 of approximately 35 degrees. The taper of the teeth 66 is believed to help maintain the teeth 66 in sliding scissors-like engagement with the right major surface and cutting portion 28 of the side plate 18. The taper of the teeth 66 also helps to strengthen the teeth 66, since the teeth 66 are thicker in their radially inward direction. In any event, the cast shell 16 preferably tends to urge the cutting blade 24 in the direction toward the side plate 18 to help maintain the teeth 66 in sliding scissors-like engagement with the cutting portion 28 of the side plate 18.

The cutting blade 24 may conveniently have an outer diameter of approximately 55 mm, and an enlarged annular hub portion 72 having an outer diameter of approximately 20 mm. The leading edges 74 (FIG. 4) of the teeth 66 are preferably formed at an angle A-5 of approximately 20 degrees with respect to radial lines extending radially outwardly from the axis of rotation of the cutting blade 24. The cutting blade 24 shown in FIG. 4 is designed to be rotated in the clockwise direction in the figure so that the teeth 66 move across the notch 20 toward the cutting portion 28 of the side plate. The leading edges 74 are skewed at the angle A-5 in the trailing direction (counterclockwise in FIG. 4) radially outwardly along the cutting blade 24.

The length of the leading edges 74 may be approximately 10 mm, and the teeth 66 are preferably slightly thicker along their leading edges 74 than along their trailing portion (e.g., between the leading edge 74 of one tooth 66 and the leading edge 74 of the next tooth 66. The teeth 66 are most preferably tapered in the trailing circumferential direction (counterclockwise in FIG. 4) from their leading edges 74 in order to prevent binding of the trailing portions of the teeth 66 in the material of the cast 12.

The assembly 10 preferably cuts the cast 12 by simultaneously functioning both as a "saw" and as "shears". That is, the teeth 66 of the cutting blade 24 "saw" through the rigid shell 16 of the cast 12 by removing small portions of the material of the shell 16, and the teeth 66 of the cutting blade 24 "shear" the soft wrapping 14 by tensioning and shearing the wrapping 14, and possibly a portion of the shell 16, between the cutting portion 28 of the side plate 18 and the teeth 66 of the blade 24. The "saw" mechanism involves the removal of cast material by continually removing material from the shell 16 with the teeth 66, and the "shear" mechanism involves tensioning the wrapping 14 between the cutting portion 28 of the side plate 18 and the teeth 66 of the cutting blade so that either the cutting portion 28 or the teeth 66 sever the wrapping 14. As used herein, "sliding scissors-like engagement" refers to the sliding engagement between the teeth 66 of the cutting blade 24 and the cutting portion 28 of the side plate 18 that facilitates shearing the soft wrapping 14.

Figure 6:
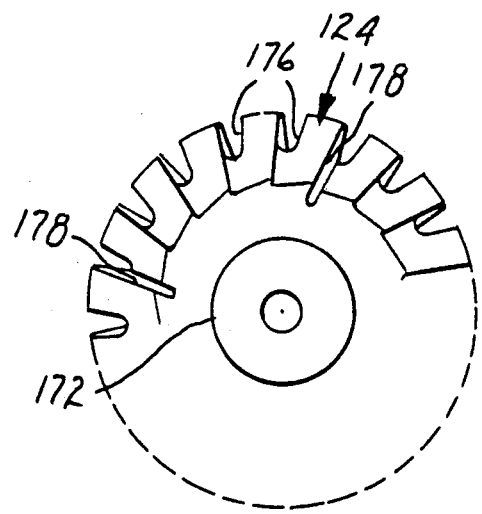
FIG. 6 is a right side elevation of a second embodiment of a cutting blade of the invention.

FIG. 6 illustrates a second embodiment of a cutting blade 124 of the invention wherein the plurality of elongate teeth 166 extend generally radially outwardly, and define a plurality of elongate slots 176, 178 extending generally radially inwardly of the cutting blade 124. The slots 176, 178 are adapted to receive a portion of the cast 12 to shear the cast 12 between the teeth 166 and the cutting portion 28 of the side plate 18. Four of the slots 178 preferably extend radially inwardly farther than the other slots 176. For example, the longer slots 178 may have lengths that are approximately twice the lengths of the shorter slots 176. As is the case with cutting blade 24, the teeth 166 of the cutting blade 124 are tapered in the radially outward direction, and the cutting blade 124 includes an enlarged annular hub portion 172.

As illustrated in FIGS. 7 and 8, a cast separator generally designated 80 may be mounted on the side plate 18 rearwardly of the notch 22. The separator 80 is adapted for spreading portions of the cast 12 that have been cut in order to facilitate advancing the assembly 10 and to prevent binding of the cutting blade 24 in the cast 12. The separator 80 may be removably mounted on a rearward portion of the side plate 18 by, for example, two "Allen" or hex head bolts or any other suitable means. The separator 80 preferably includes an elongate rod portion 82 extending generally rearwardly from the side plate 18, and a guide member 84 mounted adjacent the rearward end of the rod portion 82.

The guide member 84 has an outwardly-facing annular guide channel 86 for receiving the portions of the cast 12 that have been cut. As shown in FIG. 8, the guide channel 86 is positioned along a common plane with the longitudinal axis of the arcuate channel 60 and notch 22 of the side plate 18. Alternatively, two outwardly-facing guide channels (not shown) may be provided. Such guide channels would preferably form a wedge shaped structure having an angle of divergence substantially equal to the angle A-2 of the taper of the arcuate channel 60.

In operation, the assembly 10 is used to cut through the cast 12 as illustrated in FIG. 3. A portion of the cast 12 is introduced into the notch 22 of the side plate 18 and into contact with the teeth 66 or 166 cutting blade 24 or 124, with the finger 34 of the side plate 18 separating the cutting blade 24 from the patient 40. The cutting blade 24 or 124 is then rotated relative to the cutting portion 28 of the side plate 18 by manually reciprocating the crank arm 26, while traction is manually maintained on the handle 64 as illustrated by the arrow 88 in FIG. 1 to advance the assembly 10 forwardly through the cast 12 as the cutting blade 24 or 124 is shearing the cast 12. After the cast 12 has been cut, it may be removed from the patient 40.

The cutting blade 24 or 124 is preferably rotated in the direction wherein the teeth 66 or 166 move across the notch 22 in the direction toward the cutting portion 28 of the finger 34. The cutting blade 24 or 124 may conveniently (1) cut the rigid shell 16 by removing material therefrom with its teeth 66 or 166 in the manner of a saw blade, (2) grab and tension the wrapping 14, and possibly a portion of the shell 12, with its teeth 66 or 166 against the cutting portion 28 of the side plate 18, and (3) shear or slit the wrapping 14 and the tensioned portion of the shell 12 between the cutting blade 24 or 124 and the cutting portion 28 of the side plate 18 in the manner of a pair of scissors.

It will be observed that the illustrated assembly 10 is adapted for right handed operation, with the operator's left hand maintaining traction on the handle 64 while the right hand operates the crank arm 26. Of course, the assembly 10 could be readily adapted for left handed operation by reversing the positions of the handle 64 and crank arm 26 so that the operator's right hand maintains traction on the handle while the left hand operates the crank arm.

In addition, the cutting blade 24 or 124 could be repositioned along the "left" side of the side plate 18 so that the crank arm 26 and cutting blade 24 or 124 are along the same side of the side plate.

It is particularly contemplated that a blade guard (not shown) could be mounted or formed on the side plate 18 to cover the teeth 66, 166 of the cutting blade 24, 124. For example, an arcuate or crescent-shaped guard could be formed along the body 36 of side plate 18 with the open portion of the crescent being positioned adjacent the notch 22 of the side plate so that the teeth 66, 166 are only exposed in the notch 22.

As various changes could be made in the above constructions and methods without departing from the scope of the invention, it is intended tha all matter contained in the above description or shown in the drawing shall be interpreted as illustrative and not in a limiting sense. 5:1.12

I claim:

1. An assembly for cutting through a cast of the type typically having flexible wrapping and a rigid shell, the assembly comprising:
   a side plate having edges defining an elongate notch for receiving the cast, the edges including at least one cutting portion;
   a cutting blade rotatably mounted on the side plate adjacent the notch and in sliding scissors-like engagement with the cutting portion of the side plate to shear the wrapping and shell between the cutting portion and the cutting blade as the cutting blade is rotated; and
   means for rotating the cutting blade relative to the cutting portion of the side plate;
   the cutting blade including cutting means for saw-like removal of material from the shell to cut the shell and for scissors-like tensioning and shearing of the wrapping between the cutting portion of the side plate and the cutting blade.

2. An assembly according to claim 1 wherein the cutting blade and side plate have substantially flat surfaces in sliding scissors-like engagement, the cutting means including a plurality of elongate teeth extending generally radially outwardly of the cutting blade in sliding scissors-like engagement with the cutting portion of the side plate, with the teeth defining a plurality of elongate slots extending generally radially inwardly of the blade for receiving a portion of the cast to shear the cast between the teeth and the cutting portion of the side plate.

3. An assembly according to claim 1 wherein the cutting blade comprises a single cutting blade, and the cutting means includes a plurality of generally radially outwardly extending teeth in sliding scissors-like engagement with the cutting portion of the side plate for removing material from the shell to cut the shell and for tensioning and shearing the wrapping between the cutting portion of the side plate and the cutting blade.

4. An assembly according to claim 3 wherein the side plate has forward and rearward ends, a body and finger means extending generally forwardly from the body for placement between the wrapping of the cast and the patient to protect the patient from the cutting blade, the notch extending generally forwardly from adjacent the cutting blade, and the finger means having an edge forming the cutting portion of the side plate.

5. An assembly according to claim 4 wherein the cutting blade is of generally conical or frustoconical configuration having a base providing a substantially flat surface of the cutting blade in sliding scissors-like engagement with the cutting portion of the side plate.

6. An assembly according to claim 4 wherein the cutting blade has a recess therein generally adjacent the flat surface of the side plate for receiving material removed from the cast.

7. An assembly according to claim 4 wherein the means for rotating the blade comprises:
   an axle rotatably mounted through the side plate for rotatably supporting the cutting blade;
   a manually operable crank arm releasably mounted on the axle for rotating the axle to rotate the cutting blade relative to the cutting portion of the side plate; and
   a ratchet mechanism for ratcheting the crank arm relative to the axle;
   the side plate including a handle for facilitating operation of the crank arm.

8. An assembly according to claim 7 further comprising a separator mounted on the side plate rearwardly of the notch for separating portions of the cast that have been cut, the separator having two outwardly facing channels for receiving the portions of the cast that have been cut.

9. A method of cutting through a cast of the type having flexible wrapping and a rigid shell, the method comprising the steps of:
   providing an assembly comprising a side plate having edges defining an elongate notch for receiving the cast, the edges including at least one cutting portion, and a cutting blade rotatably mounted on the side plate adjacent the notch;
   maintaining the cutting blade in sliding scissors-like engagement with the cutting portion of the side plate;
   introducing a portion of the cast into the notch of the side plate and into contact with the cutting blade, with a portion of the side plate separating the cutting blade from the patient;
   rotating the cutting blade relative to the cutting portion of the side plate to shear the wrapping and shell between the cutting portion of cutting blade;
   advancing the assembly through the cast as the cutting blade is shearing the cast; and
   removing the cast from the patient after cutting the cast.

10. A method according to claim 9 wherein the cutting blade has a plurality of elongate teeth extending generally radially outwardly, with the teeth defining a plurality of slots extending generally radially inwardly of the cutting blade; the step of introducing a portion of the cast into the notch of the side plate including introducing a portion of the cast between the teeth of the cutting blade.

11. A method according to claim 9 wherein the step of rotating the cutting blade includes:
cutting the rigid shell by saw-like removal of material therefrom with teeth of the cutting blade;
tensioning the wrapping and at least a portion of the shell between the cutting blade and the cutting portion of the side plate; and
shearing the wrapping and the portion of the shell between the cutting blade and the cutting portion of the side plate in a scissors-like action.

12. A method according to claim 11 further comprising the steps of:
providing a cast separator on the assembly; and
spreading cut portions of the cast with the separator to facilitate advancing the assembly through the cast.

* * * * *

UNITED STATES PATENT AND TRADEMARK OFFICE
CERTIFICATE OF CORRECTION

PATENT NO. : 5,020,226

DATED : June 4, 1991

INVENTOR(S) : Jean-Paul CHabbert

It is certified that error appears in the above-identified patent and that said Letters Patent is hereby corrected as shown below:

Title page - "Foreign Application Priority Data" should be reflected to show the priority from French Patent Application No. 89.05828, filed May 1, 1989.

Col. 2, line 15, "1(Boyer)" should read --(Boyer)--.

Col. 10, line 58, "of" should read --and--.

Signed and Sealed this

Seventh Day of September, 1993

Attest:

BRUCE LEHMAN

*Attesting Officer*     Commissioner of Patents and Trademarks